United States Patent [19]
Wang et al.

[11] Patent Number: 5,032,638
[45] Date of Patent: * Jul. 16, 1991

[54] BIOABSORBABLE COATING FOR A SURGICAL DEVICE

[75] Inventors: David W. Wang, Vestal, N.Y.; Leonard T. Lehmann, Fairfield, Conn.

[73] Assignee: American Cyanamid Company, Stamford, Conn.

[ * ] Notice: The portion of the term of this patent subsequent to Dec. 16, 2005 has been disclaimed.

[21] Appl. No.: 903,800

[22] Filed: Sep. 5, 1986

[51] Int. Cl.$^5$ .............................................. C08G 63/06
[52] U.S. Cl. .................................... 524/400; 528/361; 106/287.24; 260/97
[58] Field of Search ...................... 528/361; 524/400; 106/287.24

[56] References Cited

U.S. PATENT DOCUMENTS 4,477,654 10/1984 Holmes et al. ..................... 528/361
4,562,246 12/1985 Stageman .......................... 528/361

Primary Examiner—Earl Nielsen
Attorney, Agent, or Firm—David A. Warmbold; Charles F. Costello, Jr.

[57] ABSTRACT

A suture coating comprising a copolymer having about 60 to 80 weight percent of β-hydroxybutyrate linkages is disclosed. The remaining linkages can be at least β-hydroxyvalerate. In one embodiment, the coating is the copolymer combined with a stearoyl lactylate having the formula:

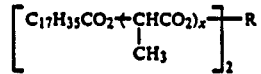

wherein X is at least two, and R is an alkaine-earth metal.

2 Claims, No Drawings

BIOABSORBABLE COATING FOR A SURGICAL DEVICE

BACKGROUND AND SUMMARY OF THE INVENTION

This invention relates to a coating and lubricating finish for surgical devices, preferably for multifilament biosorbable sutures.

It is known that suture materials are often coated with various substances to improve their handling characteristics, e.g. the U.S. Pat. Nos. 4,532,929; 4,201,216; 4,185,637; and 4,027,646 teach the use of a composition comprising a fatty acid salt or ester as a suture coating. Also, U.S. Pat. No. 4,047,533 describes the use of a water soluble poly(alkylene oxide) as a coatings for a multi-filament bioabsorbable suture. A survey included in U.S. Pat. No. 4,047,533 outlines several other approaches which are useful in improving suture knot trying performance. All of these patents are incorporated herein by reference. In summary, there is a constant research effort in the coating field to improve suture handling characteristics.

It has been discovered that a commercially available bio-polymer is useful as a suture coating. The bio-polymer can be obtained from ICI, Ltd., U.K. or from Poly-sciences Inc., Warrington, PA. For a description of the polymer, see published European patent applications Nos. 104,731; 91,224; and 69,497; and U.K. Pat. No. 2,120,671, all of which are incorporated herein by reference.

The polymer can consist of a homopolymer of hydroxy butyrate linkages, or a copolymer having approximately 70 or 80% hydroxy butyrate linkages and the remainder hydroxy valerate linkages. The homo- and copolymer can be manufactured by a bio-mass fermentation process.

The coating formulation uses methylene chloride as a solvent.

An object of this invention is to provide bioabsorbable, water insoluble coatings for multifilament sutures or bioimplantable devices. The preferred coating systems may be applied to any suture material where it is desired to improve fiber lubricity, suture knot run-down characteristics and the like. The coating is particularly useful with synthetic absorbable multifilament sutures composed of polyactide, polyglycolide, copolymers of lactide and glycolide, copolymers of glycolide and trimethylene carbonate, poly(p-dioxanone), poly(alkylene oxalate), and copolymers of glycolide and alkylene oxides, etc. Poly($\beta$-hydroxybutyrate)s are bioabsorbable materials.

The coating composition could be poly($\beta$-hydroxybutyrate) or polymers and copolymers represented by the following general structural units:

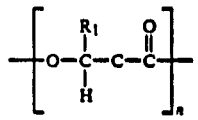

wherein each $R_1$ is a lower alkyl group, preferably methyl. U.S. Pat. No. 4,372,311 (Potts) teaches the use of poly($\beta$-hydroxybutyrate) as a coating material for water soluble disposable articles. However, the potential of using poly($\beta$-hydroxybutyrate) and its copolymers as coatings for bioabsorbable surgical devices was not disclosed. In this invention, the poly($\beta$-hydroxybutyrate) and its copolymers are specifically used to coat water insoluble surgical sutures and devices to improve their handling characteristics and biocompatability.

A bioabsorbable coating for a surgical device has been invented. The coating comprises a copolymer having about 60 to 80 weight percent of $\beta$-hydroxybutyrate linkages. In one embodiment the inherent viscosity of the copolymer measured at 30° C. on a 0.5 percent weight per volume solution of the copolymer in hexafluoroacetone sesquihydrate is about 1.5 to 5.0. In a specific embodiment, the inherent viscosity is up to about 4.0.

A coating for a bioabsorbable suture has been invented. The coating comprises a bioabsorbable copolymer having about 60 to 80 weight percent of $\beta$-hydroxybutyrate linkages and the remaining linkages comprising at least $\beta$-hydroxyvalerate. In one embodiment, the inherent viscosity of the copolymer measured at 300° C. on an 0.5 percent weight per volume solution of the copolymer in hexafluoroacetone sesquihydrate is about 1.5 to 4.0. In another embodiment, the in vivo absorption time is about one year.

Finally, a coating for a synthetic bioabsorbable suture has been inserted. The coating comprises a bioabsorbable copolymer having up to about 60 to 80 weight percent of $\beta$-hydroxybutyrate linkages and the remaining linkages comprising $\beta$-hydroxyvalerate. The copolymer has an inherent viscosity of about 1.5 to 5.0 measured at 30° C. on a 0.5 percent weight per volume solution of the copolymer in hexafluoroacetone sesquihydrate. The coating further comprises the copolymer in combination with a stearoyl lactylate having the formula:

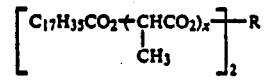

wherein X is at least two, and R is an alkaline-earth metal. In a specific embodiment, X is two and R is calcium

DESCRIPTION OF THE PREFERRED EMBODIMENT

The polymeric coatings can be applied on sutures, preferably multifilament bioabsorbable sutures or surgical devices by solution or melt coating. To achieve specific desired properties, these coating polymers can further be plasticized by various agents such as glyceryl triacetate, butyl citrate, ethyl benzoate, dibutyl phthalate, etc. Various additives can also be included in the formulation to improve the performance. Lubricants such as calcium stearate, or other salts of fatty acids, calcium stearoyl lactylate, magnesium stearoyl lactylate, bioabsorbable polyester salts, bioabsorbable polyester-carbonate salts and the like can be used. Water soluble lubricants such as poly(alkylene oxide) can also be included to provide good lubrication for suture braids.

The preferred coating polymers are poly($\beta$-hydroxybutyrate-co-$\beta$-hydroxyvalerate) and poly($\beta$-hydroxybutyrate). When used as a coating material, poly($\beta$-hydroxybutyrate)s improve the knot "run-down" performance of multifilament sutures. The polymers can also be used as binders to hold lubricants in place on the surface of a suture in order to resist displacement of the lubricant caused by friction during the knotting process. This system provides improved performance over water soluble lubricants. Tests indicate poly($\beta$-hydroxybutyrate-co-$\beta$-hydroxyvalerate) and mixtures of the polymer with calcium salts such as calcium stearate or calcium stearoyl lactylate are promising coating materials for polyglycolic acid braid. They perform well under both dry and wet conditions.

The method and the product of the present invention are further illustrated by the following examples.

EXAMPLE I

Poly($\beta$-hydroxybutyrate-co-$\beta$-hydroxyvalerate), hereafter synonomously abbreviated as "polymer" or "PHB-PHV", was commercially obtained from ICI, Ltd., UK and then placed into the following solutions:

Coating Formulation 1
0.45 grams of polymer
0.70 grams of Xylene
0.60 grams of Methylene Chloride Coating Formulation 2
6.0 grams of Calcium Stearoyl -2-Lactylate (Verv ™)*
1.6 grams of polymer
9.0 grams of Xylene
80.0 grams of Methylene Chloride
*C.J. Patterson Co., MO, U.S.A.

A 20' length of size 2/0 polyglycolic acid braid (hereinafter also abbreviated as PGA) braid coated with formulations 1 and 2 was formed into a skein and immersed in each of these solutions for 5 minutes. The skeins were then removed, allowed to drain, and were drain for 1 hour. The dried strands were then separated and cut into suitable lengths.

Each length was then tied around a conventional tubular rubber tying board as follows:

A single throw was made and then run down to the tubing to assess the resistance of the knot to rebound (the ability of the single throw to remain in position after the run-down is complete). A square knot was then formed and run down to the tubing to assess the stick-slipping of the knot (chatter) as it runs down and to assess the force required to initiate and sustain the run-down.

The rating system used to evaluate these coatings was:

Excellent
 (a) No stick-slip during run down.
 (b) Moderate force required which does not result in damage to the sleeve fibers of the suture.
 (c) No rebound of the single throw.
Good
 (a) No stick-slip during run down.
 (b) Run-down force is a little high, but no damage is done to the sleeve fiber.
 (c) Minor rebound of the single throw.
Fair
 (a) Some stick-slip during run down.
 (b) Run-down force is somewhat high and minor damage to the sleeve fiber is noted.
 (c) Minor rebound of the single throw can occur.
Poor
 (a) High stick-up in run down.
 (b) High damage or even breaking of the strand occurs.
 (c) High rebound of the single throw occurs.

The suture strands coated with formulations 1 and 2 were both rated between good and excellent.

EXAMPLE 2

The PHB-PHV of Example 1 was formulated with calcium stearoyl lactylate as follows:
Coating Formulation 3
4.0 grams PHB-PHV 70/30 polymer
4.0 grams of Calcium Stearoyl Lactylate (Verv ™),
16.84 grams Xylene (19.6 cc)
175.16 grams Methylene Chloride (133.1 cc)

All liquids are added to preweighed solids and the mixture is shaken for six hours at room temperature to get solubility and dispersability of the Lactylate.

A description of the coating method for the above suture and coating formulations is as follows. A commercially available coater (e.g. from the Bouligny Co., U.S.A.) is set to operate on a filament traveling at a speed of 50 feet per minute. The calculating air in the drying oven is adjusted to be 80° C.

There is only one pass of the filament through the capillary coating apparatus, and then through the drying oven. The coating pump is adjusted to give about 5 to 8 drops per minute at the capillary apparatus.

Using the above coating method, the percent pick up is about 3.5 to 3.6 percent based on the weight of the filament. It is to be understood that this amount of pick-up can be increased or decreased by any person skilled in the art without undue experimentation by adjusting the above parameters. Preferably, the amount of pick-up is increased by decreasing the amount of solvent in the formulation, and vice versa.

EXAMPLE 3

PGA sutures coated with PHB-PHV were tested for bacterial endotoxins. Bacterial endotoxins are also called "pyrogens" since they will elicit a fever response when introduced into the body in significant quantity.

Ten sutures were removed from their package in a manner so as not to introduce extraneous endotoxins, and washed in 100 millimeters of a sterile water diluent (1:10 dilution) for one hour at room temperature. A 1:10 dilution is considerably less than the maximum dilution (1:40) allowed by the United States Pharmacopeia XX. Endotoxins, if present, would therefore be removed from the surface of the coated suture.

The wash fluid was then tested for bacterial endotoxins by the in vitro LAL test and found negative. Considering the sensitivity of the reagent to detect endotoxins (0.06 Endotoxin Units (EU)/ml) and the dilution factor (1:10), less than 0.6 EU of endotoxin were found on one suture strand. This level would not theoretically produce a pyrogenic response.

We claim:

1. A coating for a synthetic bioabsorbable suture comprising a bioabsorbable copolymer having up to about 60 to 80 weight percent of $\beta$-hydroxybutyrate linkages and the remaining linkages comprising $\beta$-hydroxyvalerate, said co-polymer having an inherent viscosity of about 1.5 to 5.0 measured at 30° C. on a 0.5 percent weight per volume solution of the copolymer in hexafluoroacetone sesquihydrate, said copolymer in combination with a stearoyl lactylate having the formula:

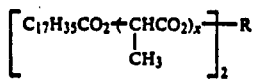

wherein X is at least two, and R is an alkaline-earth metal.

2. A coating of claim 1 wherein X is two and R is calcium.

* * * * *